United States Patent [19]
Akbar et al.

[11] Patent Number: 5,439,580
[45] Date of Patent: Aug. 8, 1995

[54] SOLID-STATE GAS SENSOR FOR CARBON MONOXIDE AND HYDROGEN

[75] Inventors: Sheikh A. Akbar; Abdul M. Azad; Lora B Younkman, all of Columbus, Ohio

[73] Assignee: The Ohio State University, Columbus, Ohio

[21] Appl. No.: 147,711

[22] Filed: Nov. 5, 1993

[51] Int. Cl.$^6$ .............................. G01N 27/26
[52] U.S. Cl. .................... 204/425; 204/424; 422/83; 422/94; 422/98
[58] Field of Search .......... 204/424, 425, 426, 153.16, 204/153.17, 153.18; 338/34; 73/71.5; 422/83, 94, 98; 501/152, 134, 103, 104, 105

[56] References Cited

U.S. PATENT DOCUMENTS

| | | | |
|---|---|---|---|
| 3,886,785 | 6/1975 | Stadler et al. | 338/34 |
| 3,932,246 | 1/1976 | Stadler et al. | 156/89 |
| 4,222,026 | 9/1980 | Heiney, III et al. | 338/34 |
| 4,228,128 | 10/1980 | Esper et al. | 422/98 |
| 4,324,761 | 4/1982 | Harris | 338/34 |
| 4,501,818 | 2/1985 | Rossi | 501/152 |
| 4,525,464 | 6/1985 | Claussen et al. | 501/152 |
| 4,659,680 | 4/1987 | Guile | 501/152 |
| 4,985,126 | 1/1991 | Haefele et al. | 204/153.14 |
| 5,182,136 | 1/1993 | Saburi et al. | 338/34 |
| 5,296,421 | 3/1994 | Nishida et al. | 501/105 |

Primary Examiner—John Niebling
Assistant Examiner—Bruce F. Bell
Attorney, Agent, or Firm—Frank H. Foster; Kremblas, Foster and Millard

[57] ABSTRACT

Anatase titania is used as the sensitive ceramic for sensing the amount of carbon monoxide and hydrogen in mixed gasses where the changes in electric current characteristics passing through such ceramic when it is exposed to such gases is used to determine the amount of carbon monoxide and hydrogen present. Such sensor is made selective to hydrogen when alumina is included in the ceramic and to carbon monoxide when yttria is included. Additions of a catalytic metal particularly iron or palladium is beneficial to the anatase titania-yttria ceramic in its selective sensing of carbon monoxide.

12 Claims, 12 Drawing Sheets

SOLID-STATE GAS SENSOR FOR CARBON MONOXIDE AND HYDROGEN

TECHNICAL FIELD

This invention relates to gas sensors and gas sensing materials comprising anatase titanium oxide ($TiO_2$) as the sensitive material, to anatase $TiO_2$ in combination with alumina ($Al_2O_3$) and to anatase $TiO_2$ in combination with yttria ($Y_2O_3$) for use as carbon monoxide-hydrogen, hydrogen and carbon monoxide sensing materials respectively. The anatase titania plus yttria preferably contains additionally a metal catalyst particularly iron or palladium.

BACKGROUND ART

Sensing devices employed to determine the amount of a specific gas in a mixture of gasses such as automotive exhaust are presently based on measurements of the electrical resistance of certain ceramic oxides. Such resistance changes directly reflect the amount of specific gas present. Transition metal oxides, particularly $TiO_2$ are frequently used for such application. The use of such materials for this application is disclosed in particular by U.S. Pat. Nos. 3,886,785 and 3,932,246.

Relatively pure $TiO_2$ made by solution precipitation techniques has a tetragonal crystalline structure and is called anatase titania. Titania or $TiO_2$ that is generally employed as a ceramic sensor material for sensing carbon dioxide, carbon monoxide, hydrocarbons, alcohol, fumes, humidity and the like in atmosphere or to determine the carbon dioxide, carbon monoxide, oxygen, nitrous oxide and sulfur dioxide contents of automobile exhausts employ a nontetragonal crystalline titania called rutile titania. In the fabrication of the sensors of U.S. Pat. Nos. 3,886,785 and 3,932,246 anatase titania is converted to rutile titania for this application.

It has now been discovered that anatase titania sensors are particularly useful in the determination of carbon monoxide and hydrogen in gases particularly at elevated temperatures (up to about 850° C.). It has also been discovered that anatase titania in combination with alumina is selective to the determination of hydrogen in a gas mixture and that anatase titania in combination with yttria is selective to the determination of carbon monoxide, particularly when a small amount of a catalyst such as iron or palladium is included.

It is therefore an object of the present invention to provide anatase $TiO_2$ sensors useful for the determination of hydrogen and carbon monoxide in gases.

It is also an object of the present invention to provide anatase $TiO_2$—$Al_2O_3$ sensors useful for the selective determination of hydrogen in gases.

It is also an object of the present invention to provide anatase $TiO_2$—$Y_2O_3$ sensors useful for the selective determination of carbon monoxide in gases.

A further object of the present invention is to provide anatase $TiO_2$—$Y_2O_3$ sensors containing small amounts of catalysts for the selective determination of carbon monoxide in gases.

An additional object of this invention of to provide anatase-yttria sensors that contain Fe or Pd as catalysts for the selective determination of carbon monoxide in gases.

BRIEF DISCLOSURE OF INVENTION

From the viewpoint of industrial and automobile exhaust pollution control, a sensor capable of detecting and measuring the concentration of harmful gases such as, carbon monoxide and hydrogen in the ambient, is desired. This invention describes the development of a new anatase titania ($TiO_2$)-based semiconducting oxide material as a reliable and rugged CO and hydrogen gas sensor at high temperatures. Significant change in the sensing characteristic of the anatase modification of $TiO_2$ was observed when admixed with an insulating second phase, such as alumina or yttria. In the case of $TiO_2$-10 wt. % $Al_2O_3$ (designated as TA), the sensor response was found to be exclusively dependent on the hydrogen concentration alone; the presence of CO or $CO_2$ did not affect the sensitivity. On the other hand, the sensor based on $TiO_2$-10 wt. % $Y_2O_3$ (designated as TY) showed increased sensitivity to CO and decreased interference due to $H_2$, compared to that of the undoped $TiO_2$. Addition of elemental iron or palladium, in small concentration, to the two-phase mixture of anatase titania and yttria further improves the sensitivity and selectivity of the latter to CO. This material (designated as TYF) possesses excellent sensitivity and selectivity to carbon monoxide, reasonably good thermal stability and sufficiently long shelf-life in environments containing CO gas in concentrations ranging from several ppm to about 5% by wt. Neither TA nor TY showed any interference from $NO_x$. Palladium additions to the two-phase matrix TY is preferred over the iron addition owing to its better oxidation resistance, pronounced catalytic activity and higher specificity and selectivity to CO.

This invention has enabled the development of stable, rugged and selective CO—$H_2$, CO and $H_2$ sensors, capable of operating in the temperature range of 500 to 850° C. Some of the salient features of the anatase $TiO_2$—$Y_2O_3$—Fe sensors are high selectivity, sufficiently long shelf-life for continuous use, interference in signal only with high concentrations of hydrogen (>400 ppm), excellent reversible characteristics (no external regeneration medium required), and capable of functioning as CO meter in industries (for CO up to 5%) as well as an ON/OFF type alarm device (lower limit of detection ~100 ppm) in homes, offices and other public places; with proper chemistry variation this limit could further be brought down to about 25 ppm and sensor signal (resistance) being related to CO content and temperature through simple analytical expressions can be easily translated into electronic outputs with simple associated circuitry to make it an inexpensive, portable, easy-to-handle sensing device.

DETAILED DESCRIPTION

Figure 1:
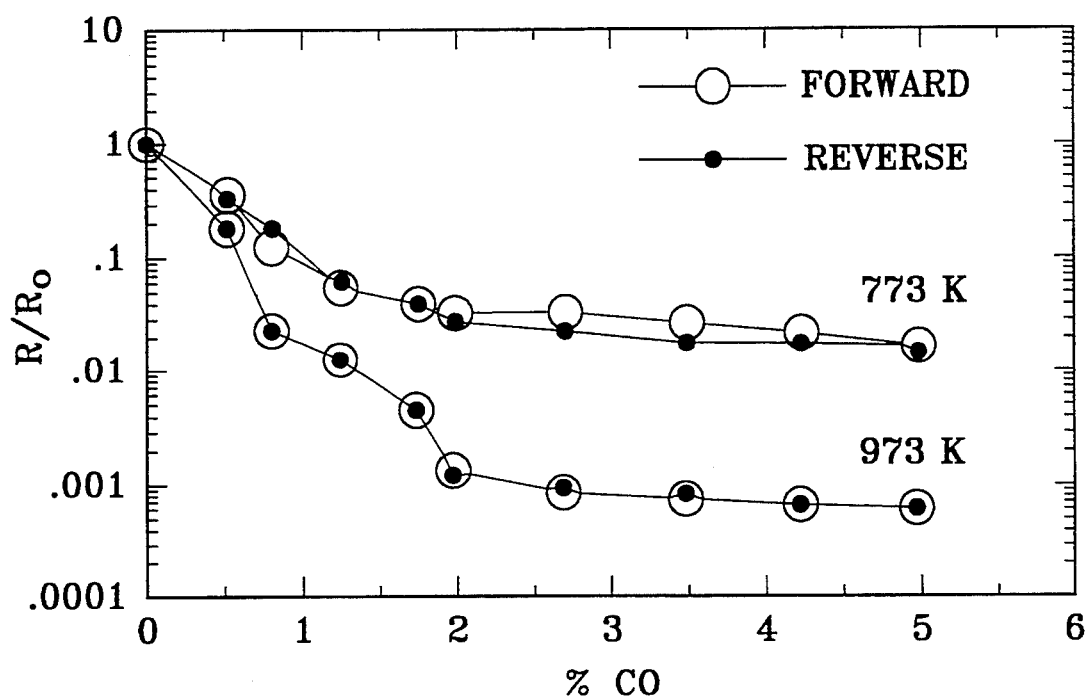
FIG. 1 is a graph showing the resistance variation of a $TiO_2$ thick film sensor as a function of CO concentration.

This invention pertains to the development and use of new oxide sensor materials, based on the anatase form of titanium dioxide. Anatase $TiO_2$ sintered powders have been found to have carbon monoxide and hydrogen sensing capabilities. When such powders are mixed with a minor quantity of alumina powder the resulting sensors have a selective sensitivity to hydrogen and when mixed with a minor quantity of yttria such combination exhibits selective sensitivity to carbon monoxide. The sensitivity of anatase titania-yttria mixtures to carbon monoxide is significantly enhanced by minor additions of catalytic metals particularly iron and palladium. Such sensors are particularly effective for the detection and metering of $CO-H_2$, $H_2$ and CO gas respectively in the ambient at temperatures ranging from 500° to 850° C.

Increased sensitivity and selectivity to carbon monoxide is particularly achieved by anatase $TiO_2$ by the addition of a minor insulating second phase yttria and a small addition of the metals iron or palladium. Particularly significant success has been achieved with 10% by wt yttria and 2%, by wt, iron or palladium A preferred composition range is from about 5% to 15%, by wt, yttria and up to about 5% by wt, iron or palladium, balance anatase $TiO_2$. Such anatase titania is preferably solution precipitated $TiO_2$ which may (or may not) contain residual impurities.

Increased sensitivity and selectivity to hydrogen is particularly achieved by anatase $TiO_2$ by the addition of a minor insulating second phase alumina. A preferred composition range is from about 5% to 15% by wt, alumina.

Samples were prepared by mixing and blending high purity, fine-grain $TiO_2$(X-ray pure "anatase" phase), high purity yttria, high purity $\alpha$-$Al_2O_3$, metallic Fe and Pd in predetermined weight ratios so as to give T, TY, TA, TYF and TYPd5. The mixture was then ball milled in isopropanol for 24 hours. Subsequently it was dried at 200° C. for 8 hours, cooled, homogenized in an agate mortar for 2 hours and sieved through a 325 mesh screen.

The sensors were made in the thick film configurations. The thick film pastes were prepared by blending powder form of sensor material (T, TY, TA, TYF, TYPb5) in 1-heptanol solvent. The sensor pastes were printed on alumina substrates using a 325 mesh screen and subsequently heated in air to burn off the solvent, leaving a compact and adhering film (approximate average thickness of 100 $\mu$m) on the substrate. Alumina was found to be an ideal substrate material for titania film, owing to the similarity between the thermal expansion coefficients of the two. Thin gold wires, attached with the help of conductive gold paint, served as electrodes. The electrical resistance was measured between 500°–850° C., as a function of CO concentration in a nitrogen stream as the background. In order to explore the reversibility of the sensor response, measurements were carried out as a function of gas concentration both in increasing and decreasing mode. Regeneration characteristics of these sensors were followed in various environments. Experiments were also done to determine the lower limit of CO detection by the sensors, using a nitrogen gas tank containing 0.55 volume percent of CO. Electrical measurements were performed several times on a single sample, to test the repeatability characteristics of the sensor material, and also on different samples to examine the reproducibility and precision of the results, Therefore, the data shown in various figures here are representative of many measurements with negligible scatter.

Figure 2:
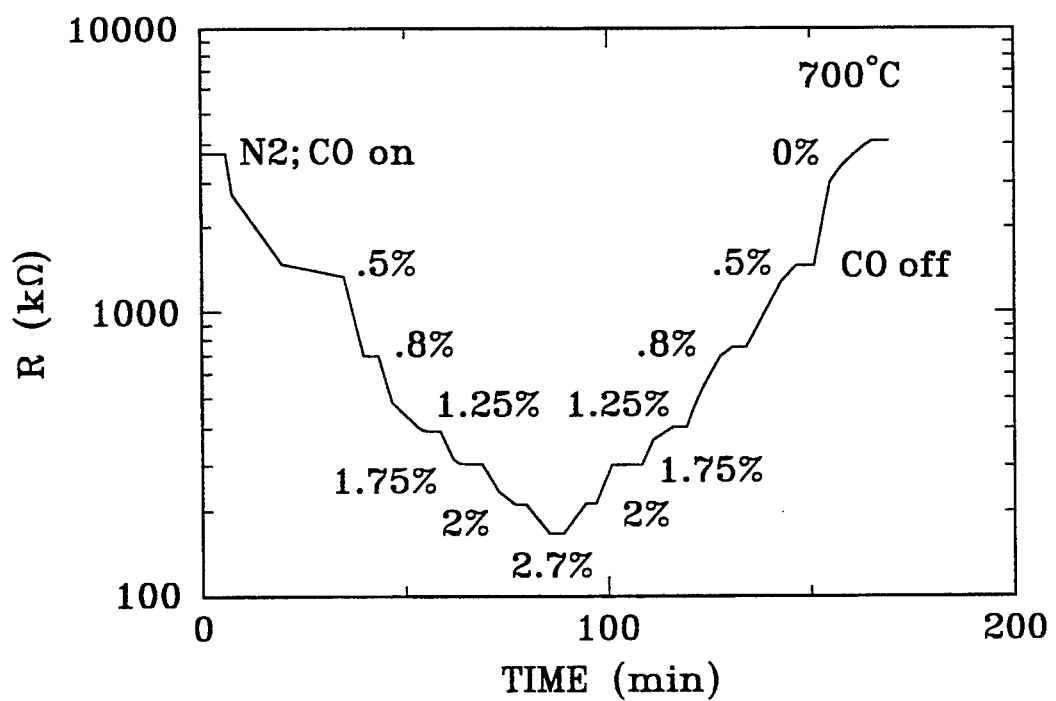
FIG. 2 is a graph showing the time dependence of the resistance response of titania sensor for various CO levels.

FIG. 1 shows the dependence of relative resistance, $R/R_o$, ($R_o$ being the resistance of the film in nitrogen), of a $TiO_2$ thick film sample on CO concentration, at 500° and 700° C. Each data point is the steady-state resistance measured after a change in the composition of the gas mixture. The resistance of the sensor changed gradually and dropped in steps with increasing CO concentrations at both the temperatures of measurement. The steps in the resistance vs. CO concentration were distinct up to about 4 volume percent of CO, beyond which the resistance did not change significantly. In addition the sensors showed good reversibility with respect to resistance response as a function of CO, particularly at 700° C. This feature is also shown in FIG. 2, as a function of time for various levels of CO at 700° C. The data points for both increasing and decreasing pressures of CO fall on the same curve, showing rapid establishment of equilibrium. This shows that the sensor could be completely regenerated, merely by shutting off the CO gas, without exposing it to any oxidizing atmosphere such as air or oxygen; this is in marked contrast to several other gas sensors based on semiconducting oxides, where regeneration of the sensor requires the oxidation by either air or oxygen.

Figure 3:
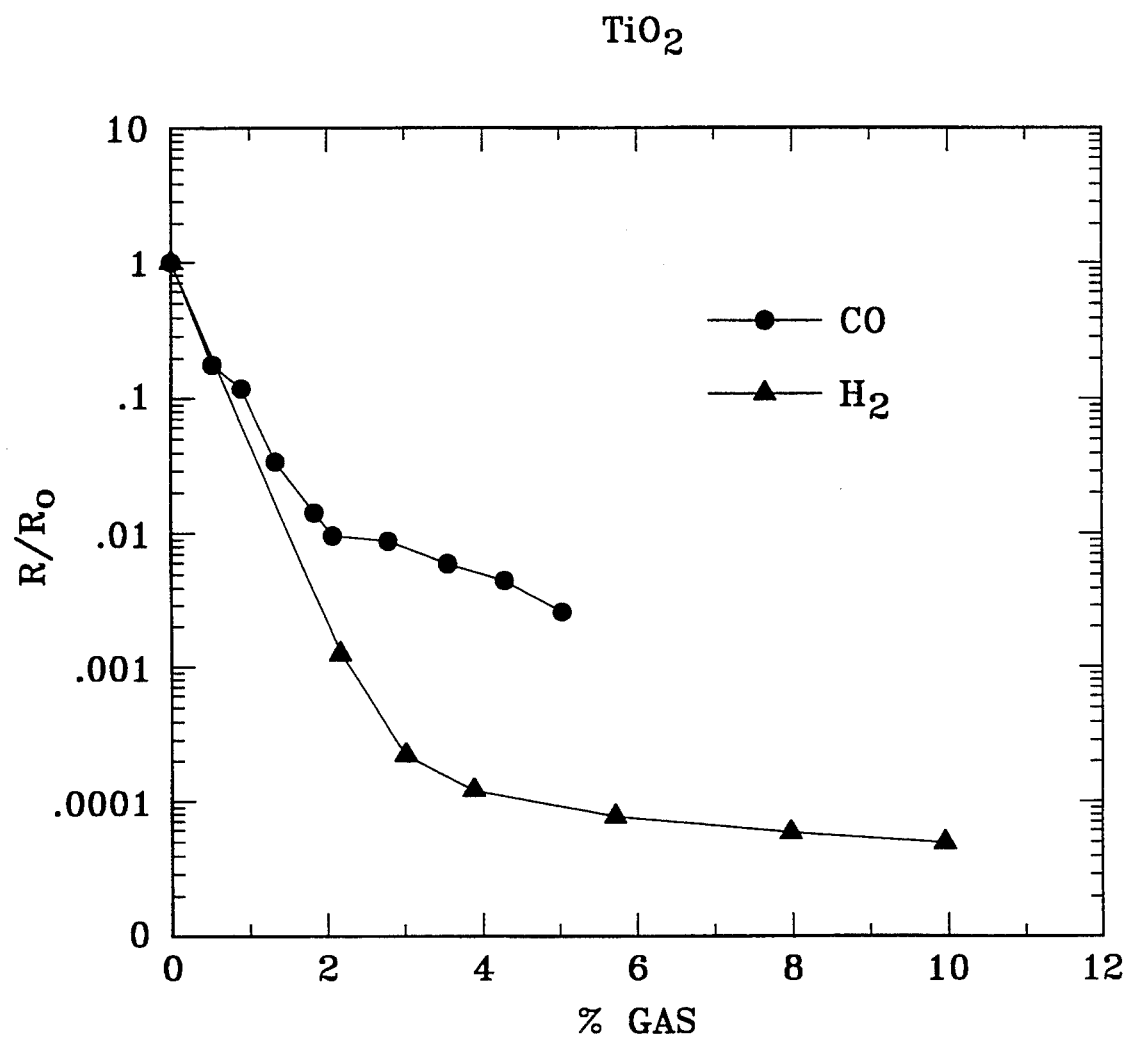
FIG. 3 is a graph showing that pure anatase $TiO_2$ is capable of sensing both CO and $H_2$.

FIG. 3 clearly illustrates that pure anatase $TiO_2$ senses both CO and $H_2$.

Figure 4:
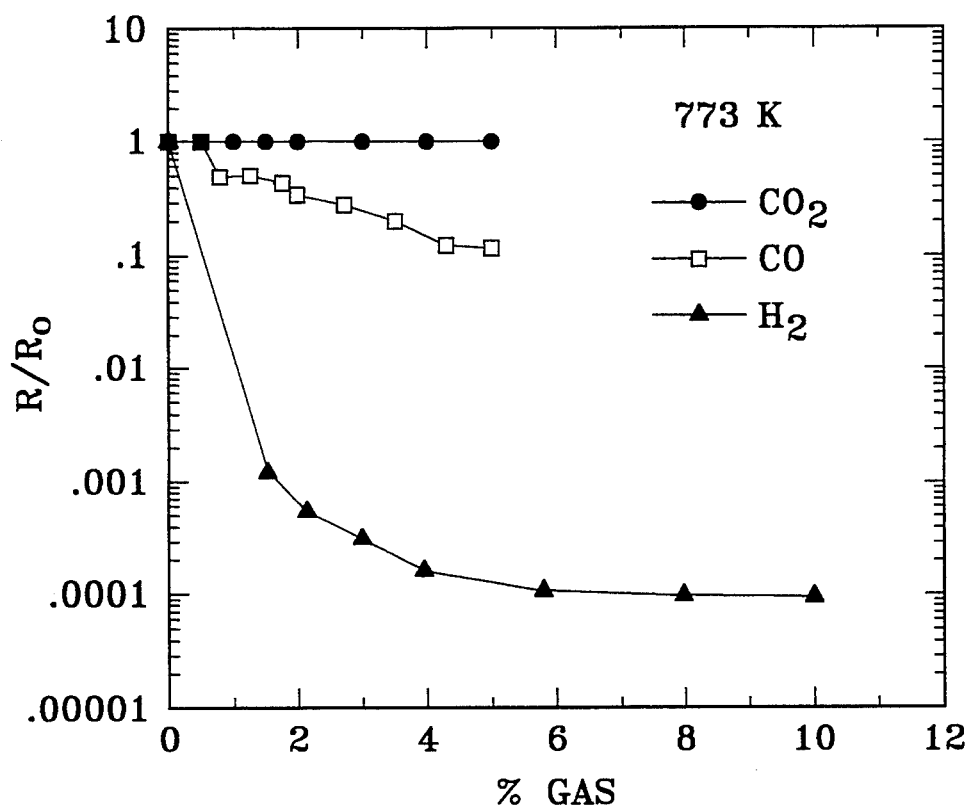
FIG. 4 is a graph showing the sensitivity of $TiO_2$-10 wt. % $Al_2O_3$ to $H_2$, CO and $CO_2$.

FIG. 4 illustrates that $TiO_2$-10 wt. % $Al_2O_3$ (TA) sensor material is practically a $H_2$ sensor with no response to $CO_2$ and very negligible response to CO.

Figure 5A:
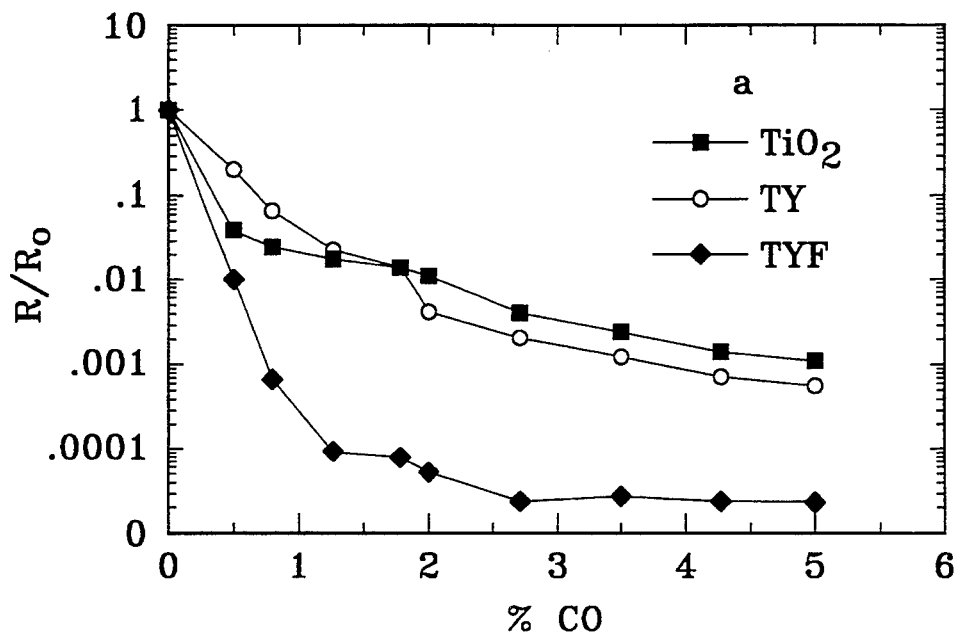
FIGS. 5(a) and 5(b) are graphs showing the sensitivity of a $TiO_2$-10 wt. % $Y_2O_3$ sensors to (a) CO and (b) $H_2$ at 500° C.
Figure 5B:
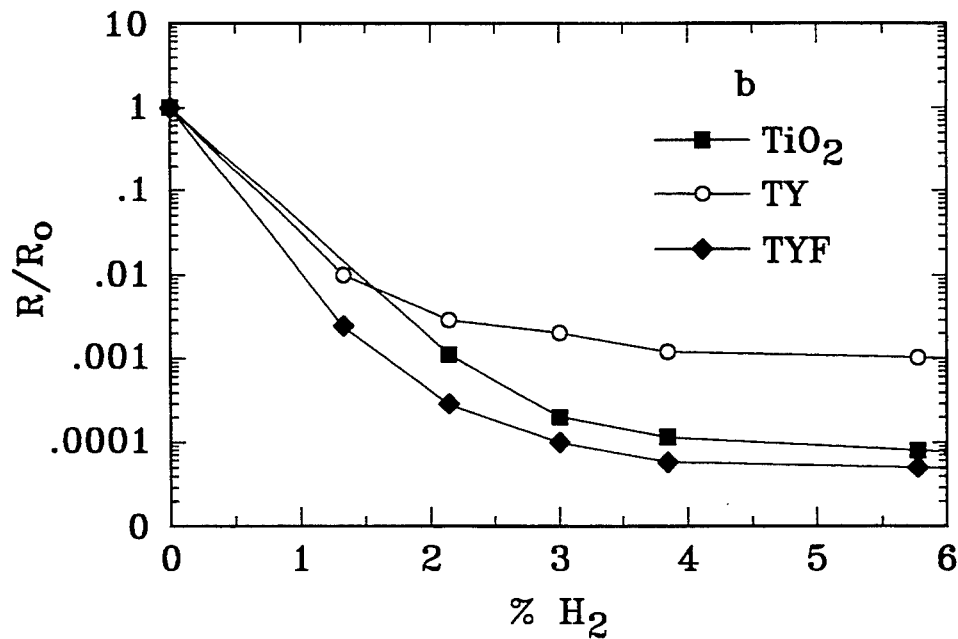
Figure 6:
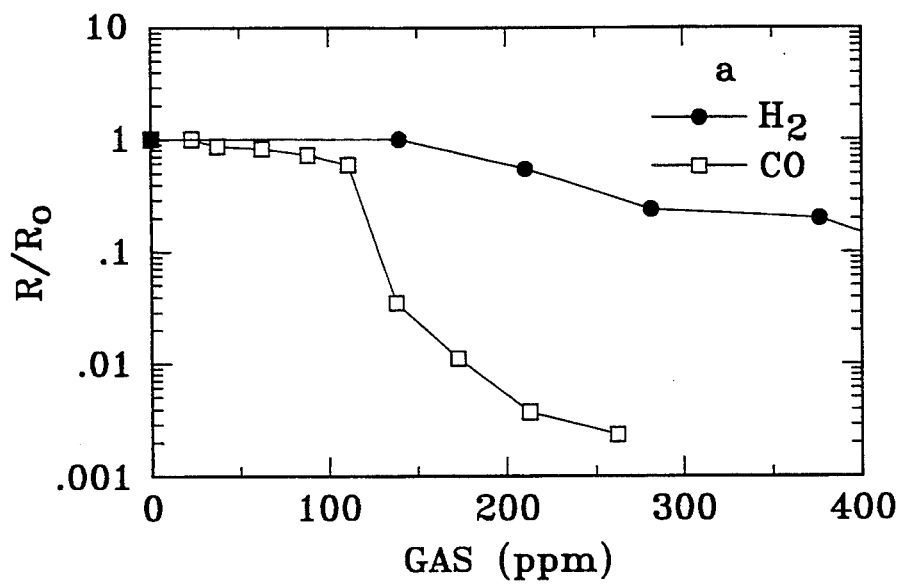
FIG. 6 is a graph showing the concentration dependence of iron-catalyzed $TiO_2$-10 wt. % $Y_2O_3$ sensor to low levels of CO and $H_2$ at 500° C.

FIG. 5a and 5b depict typical concentration dependence of the resistance of a film made from $TiO_2$- 10 wt. % $Y_2O_3$ (TY) mixture for CO and $H_2$, respectively. A comparison with the response of pure $TiO_2$ sensor, readily reveals that the sensitivity of the two phase mixture for CO remains unaffected. Addition of metallic iron greatly enhanced the sensitivity to CO, whereas the same sensitivity level towards hydrogen was maintained. This can be appreciated more clearly be referring to FIG. 6. It is evident that Fe additions to the TY mixture tunes it to detect as low as about 100 ppm of CO, whereas the presence of hydrogen in the gas stream in concentration up to about 400 ppm does not interfere with the sensitivity towards CO. The preferential detection of CO over hydrogen by iron added-TY sensor is clearly manifested.

Having established the feasibility of employing TYF as an effective high temperature (500°<T<850° C.) CO sensor, detailed research was conducted to correlate the gas concentration in the flue gas stream with the resistance of the film and the temperature. Long-term experiments were also carried out to determine the approximate shelf-life of the sensor at various temperatures when exposed to various levels of the CO gas. For this purpose, prototype sensors in two configurations (FIG. 7 and 8) were designed and tested.

Figure 7:
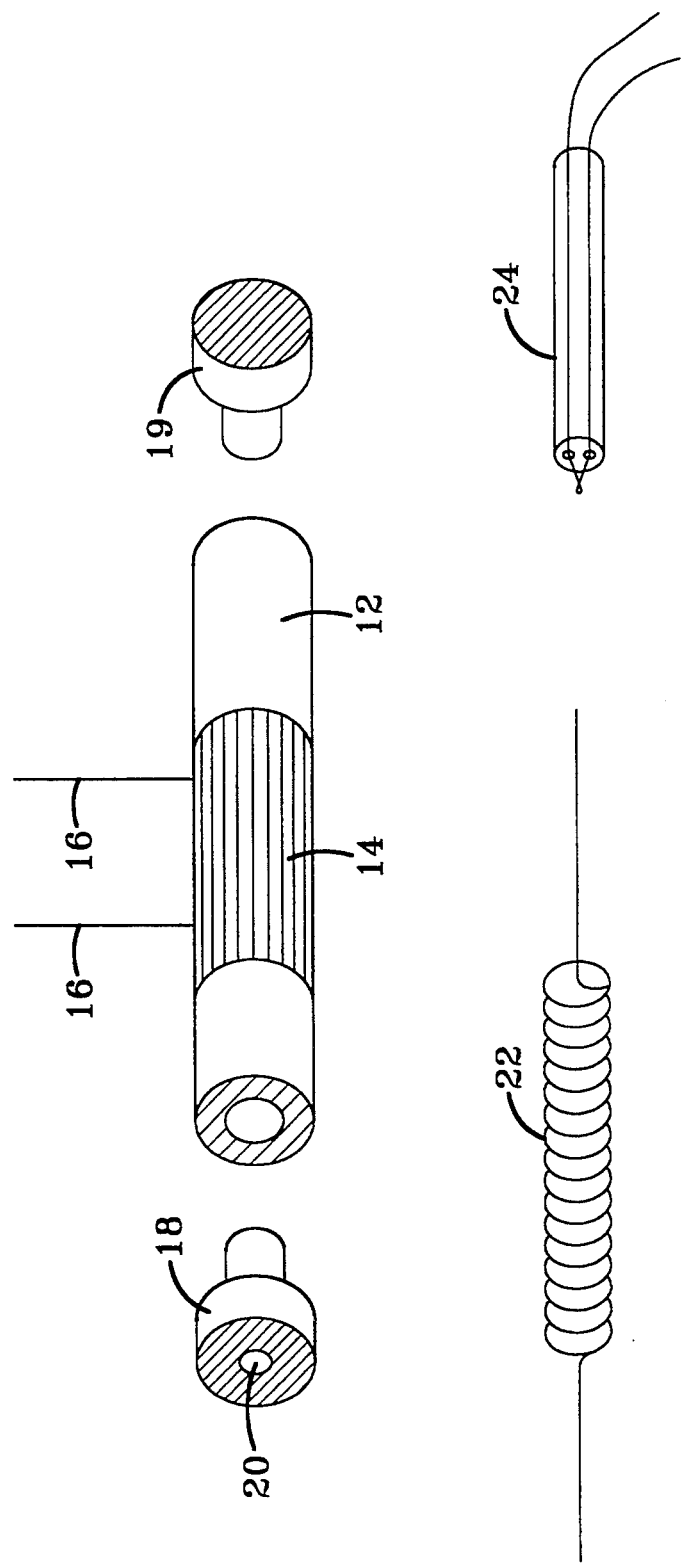
FIGS. 7 & 8 are schematic diagrams of prototype CO sensors used in the application of the materials of the present invention.

The sensor embodiment of FIG. 7 consists of a single-bore alumina tube supporting member 12 provided with an anatase $TiO_2$ 10 wt. % $Y_2O_3$, 2 wt. % Fe ceramic coating 14 (or other sintered powders as described above) and gold wire electrodes 16. Ceramic plugs or end members 18 and 19 serve to completely seal the unit except for a passageway 20 which opens into the bore of tube supporting member 12. Nicrome heater 22 and Chromel-Alumel thermocouple 24 are positioned within the bore of member 12 and their leads extended through plug passageway 20 of plug member 18.

In operation the sensor is positioned within the gas to be tested, heated to the appropriate temperature with heater 22. Electric current is imposed through the leads 16 and external monitoring devices (not shown) determine the CO content of the gas being tested.

Figure 8:
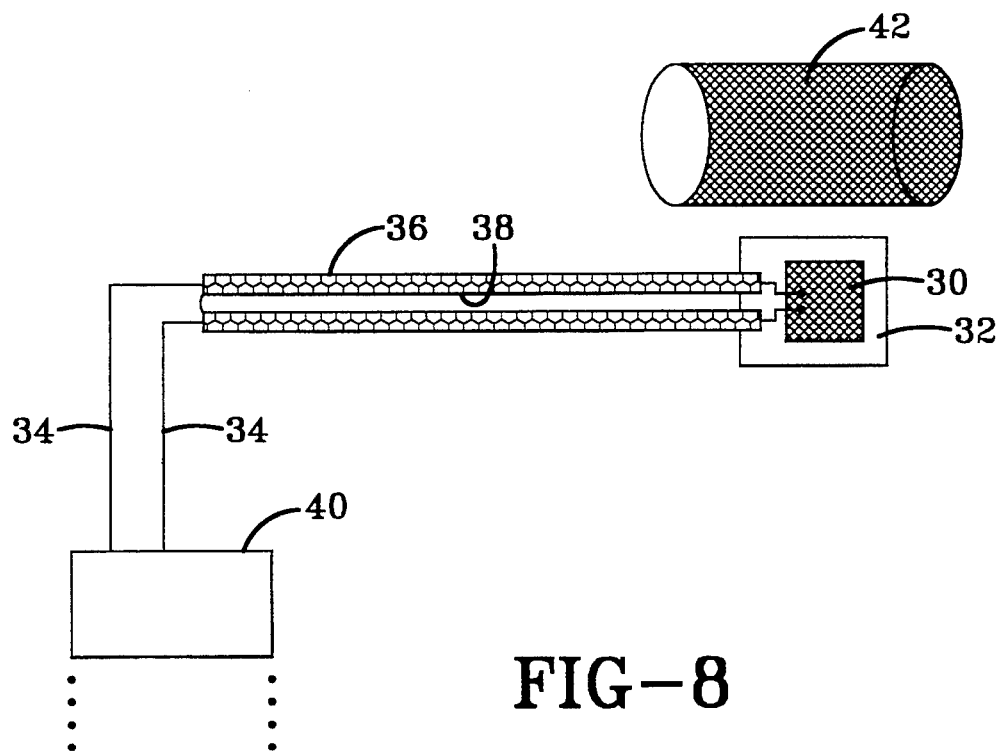

The sensor embodiment of FIG. 8 consists of a sensor film or screen 30 of anatase $TiO_2$, 10 wt. % $Y_2O_3$, 2 wt. % Fe ceramic coating (or other ceramic of the present invention) printed on an alumina support 32. Gold or platinum lead wires 34 connected to separated positions of sensor film 30 extend between twin bore aluminum tubes 36 and 38 to an electronics unit 40. Unit 40 performs the functions of the sensor system block diagram of FIG. 18 that automatically calculates the amount of CO—$H_2$, CO or $H_2$ in a gas in accordance with the changes in the current characteristics of the electric current imposed between the lead wires 34 when the ceramic 30 is exposed to the gaseous environment being tested. Protective cylindrical mesh 42 is positioned to surround support 32 and coating 30 when such members are exposed to the corrosive hot gaseous environment.

Figure 9:
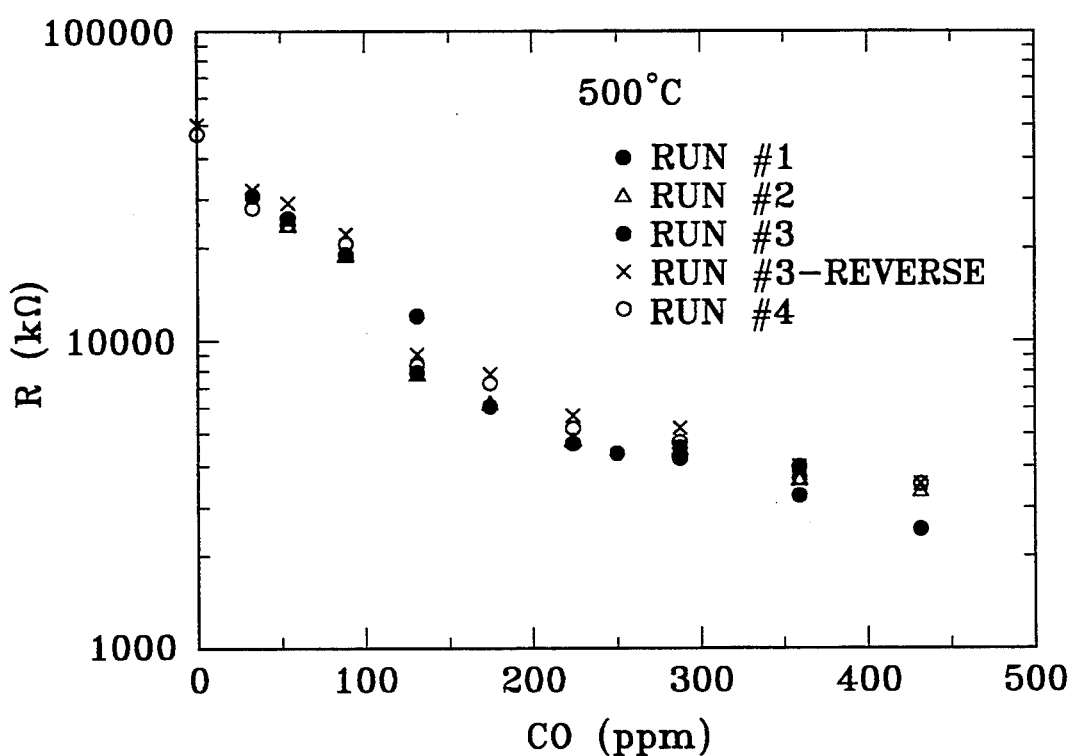
FIG. 9 is a graph showing the reproducibility trend of the response of TYF-based CO sensors in the low CO concentration range at a typical temperature of 500° C.

FIG. 9 depicts the concentration (in ppm range) dependence of the resistance of TYF films.

Figure 10:
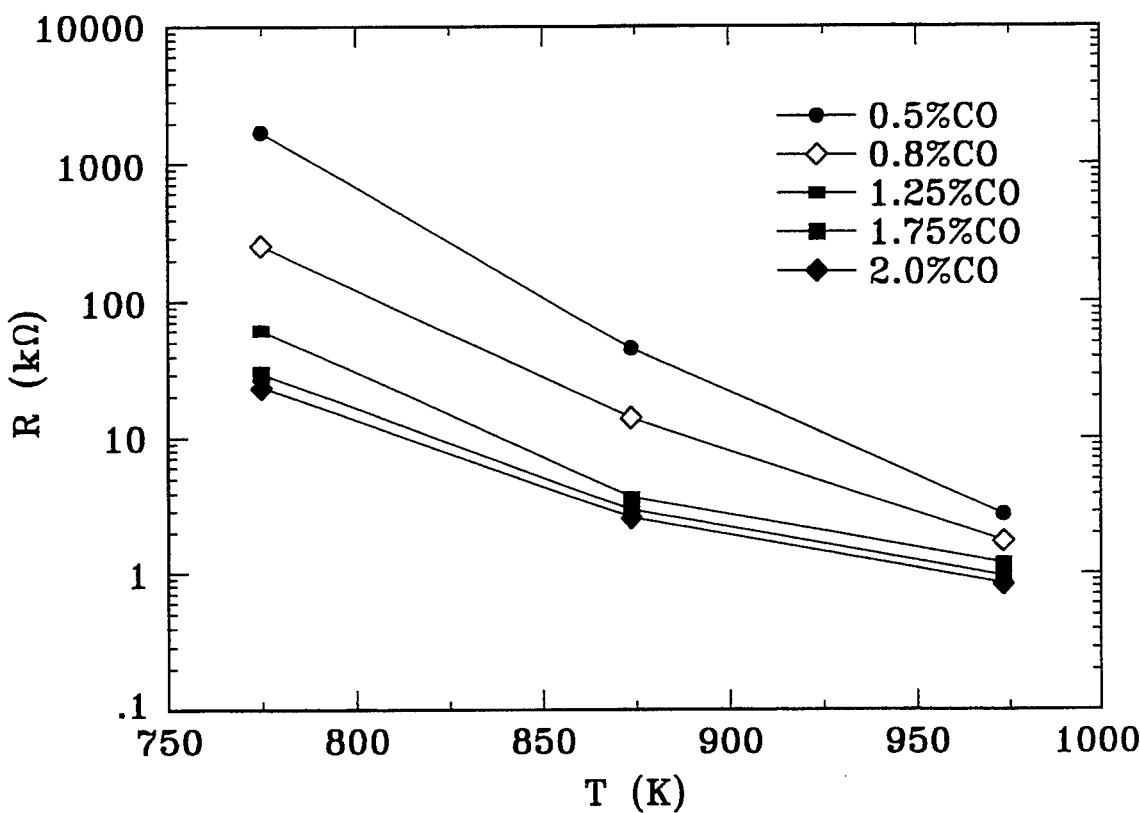
FIG. 10 is a graph showing the temperature dependence of the sensor resistance in high CO region.
Figure 11:
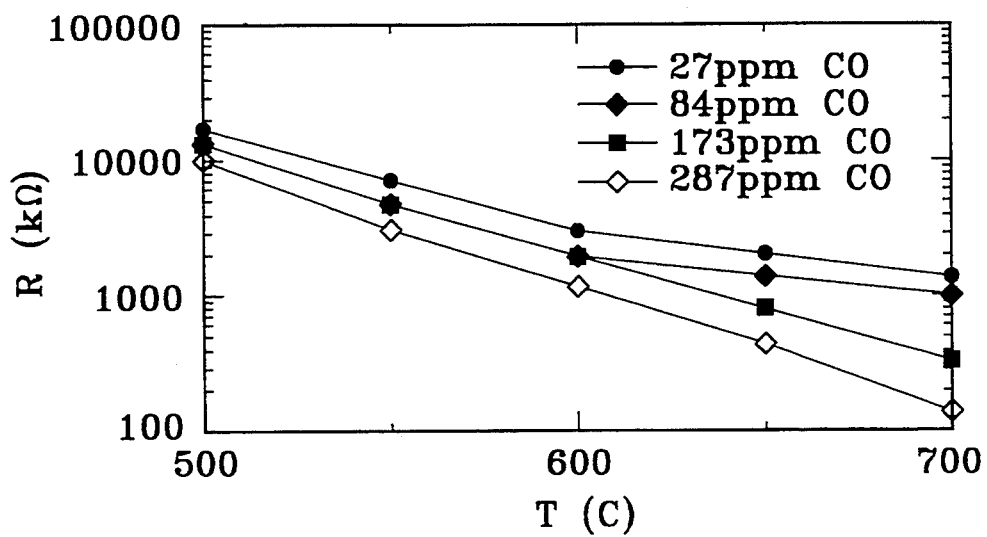
FIG. 11 is a graph showing temperature dependence of the sensor resistance in low CO region.

The cumulative data represent cyclic runs on the same sample as well as those on different samples. As can be seen from this figure, the trend in sensor behavior is consistent from sensor to sensor and also for the same sensor run on different days. The variation of film resistance as a function of temperature for given high (percent) and low (parts per million, ppm) levels of CO gas in the ambient is shown in FIGS. 10 and 11, respectively.

Figure 12:
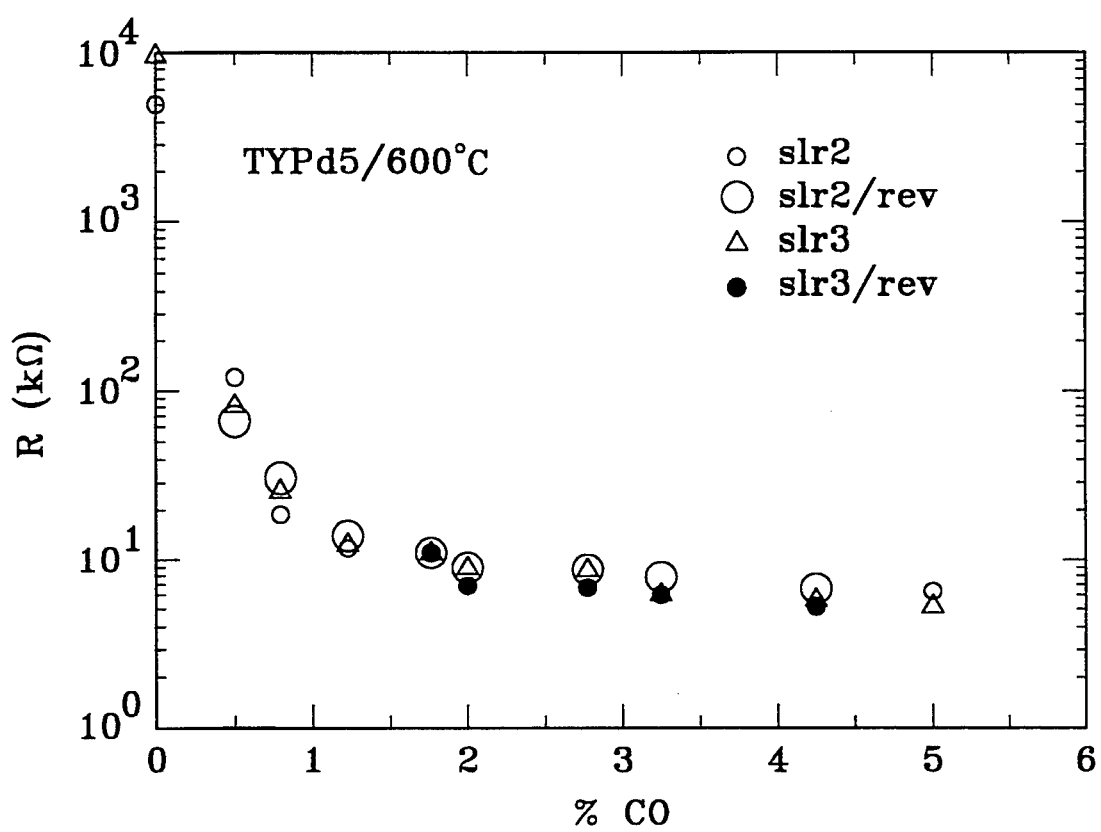
FIG. 12 is a graph showing the response behavior of Pd catalyzed titania-yttria sensors to CO gas at 600° C.

FIG. 12 shows the response behavior of Pd catalyzed anatase titania-yttria sensors to CO gas at 600° C.

Figure 13:
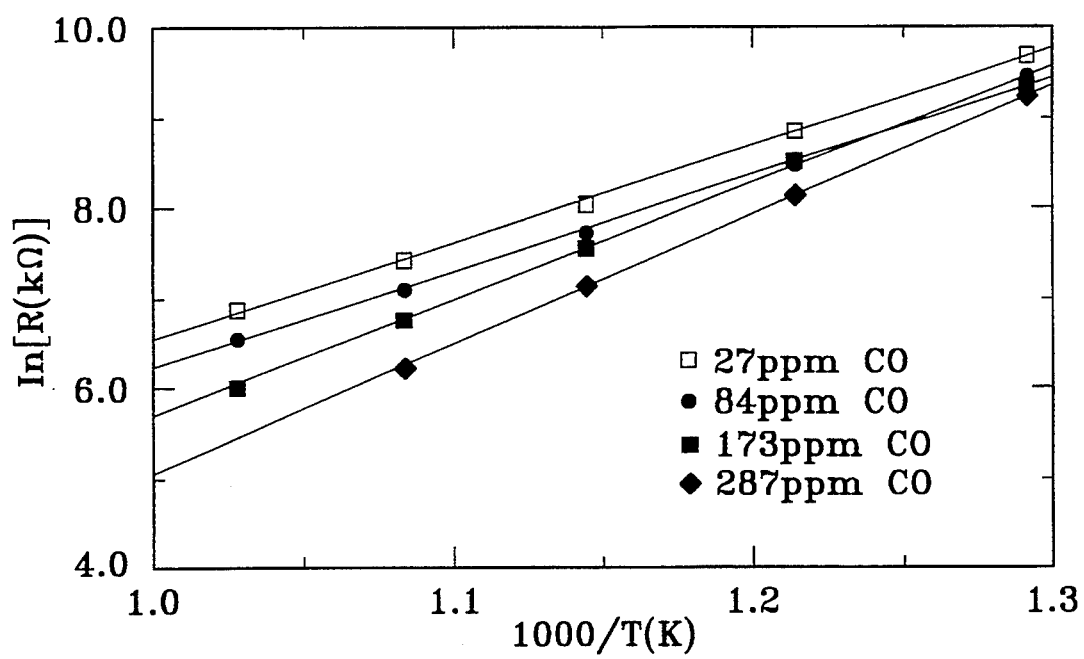
FIG. 13 is a graph showing Arrhenius plots for the sensor output for various percent level of CO gas.
Figure 14:
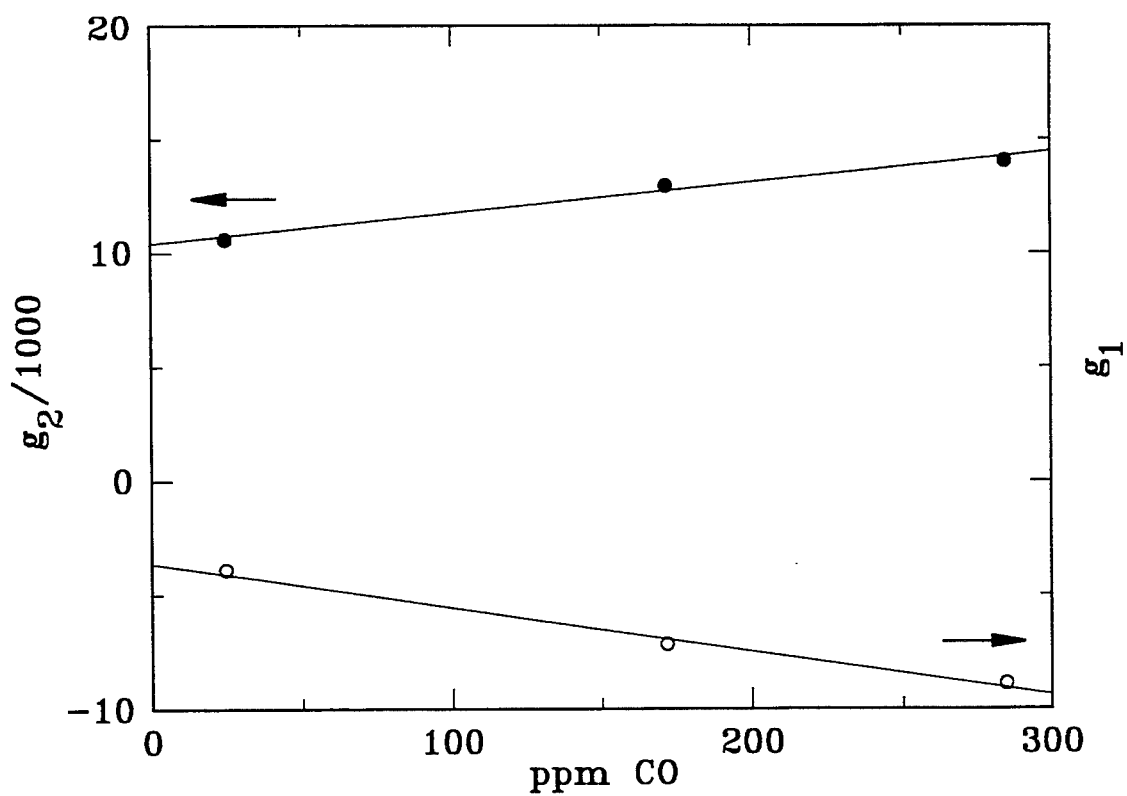
FIG. 14 is a graph showing a correlation of the fitting parameters with the concentration of CO.
Figure 15:
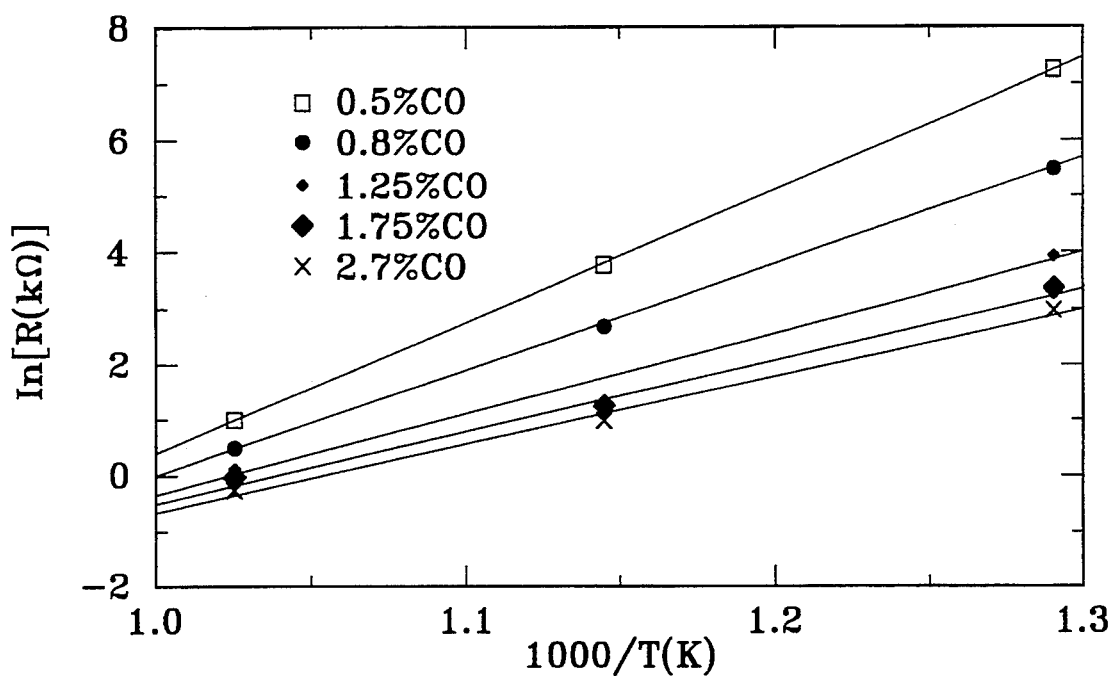
FIG. 15 is a graph showing Arrhenius plots for the sensor output for various ppm levels of CO gas.
Figure 16:
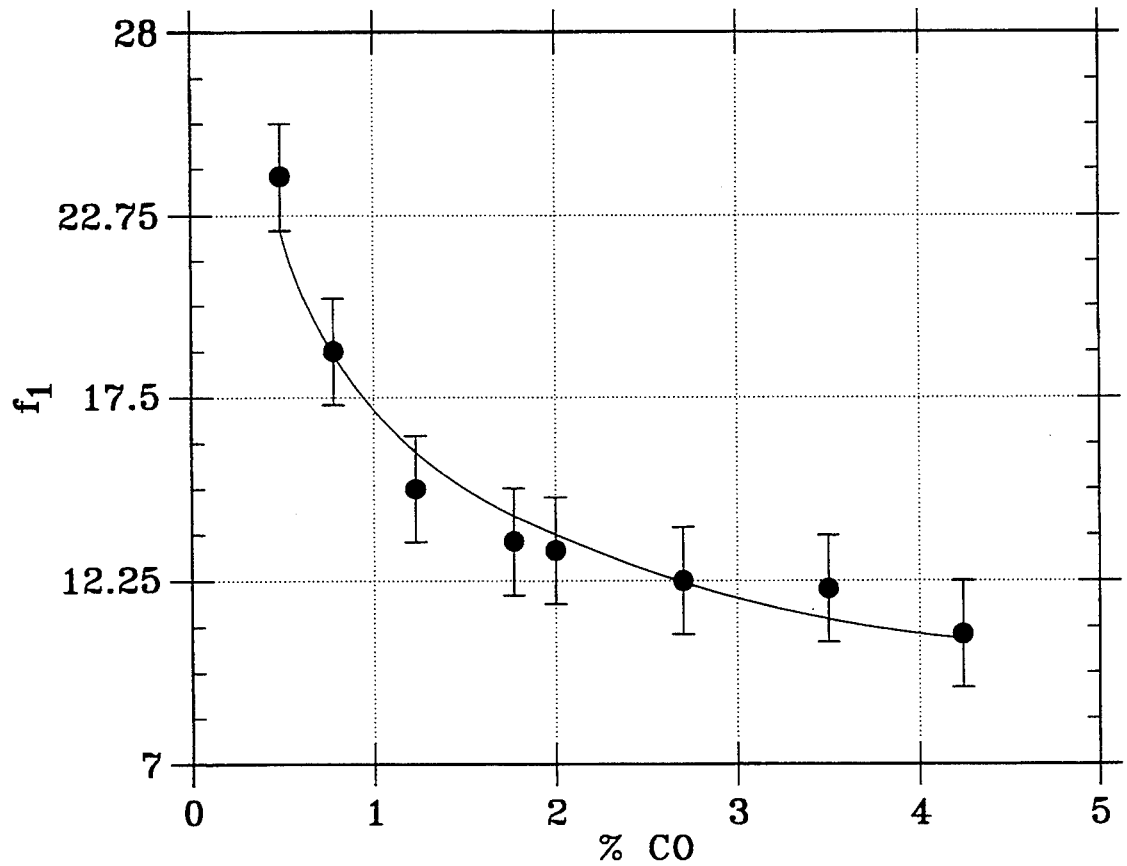
FIG. 16 is a graph showing correlation of the fitting parameters with the concentration of CO.

An approximate linear dependence of sensor resistance on the temperature is observed, which might be helpful in designing a simple electronic circuitry for the detector made of this exotic material. Plotting log (resistance) against the reciprocal temperature, however, yields a much better (almost perfect) linear fit of the observed data, for both low (ppm) and high (percent) levels of CO gas. This linear behavior of TYF is shown in FIGS. 13 and 15, respectively. Each of these straight lines could be least-squared fitted with a correlation coefficient ranging from 0.985 to 1.00. The intercepts and the slopes of each of these straight lines (In R vs. 1/T plots) showed a unique dependence on the gas concentration (FIGS. 14 and 16). With the help of these parameters, a unique correlation between the gas concentration, temperature and the resistance of the film was derived, which when incorporated into the software of the sensing device would enable one to directly determine gas concentration in the ambient at a given temperature, simply by measuring the resistance of the film.

The parametric equations for this purpose take the form:

$$\ln[R(k\Omega)] = -f_1 (1 - 1000/T(K))$$
$$f_1 = 17.312 \times C^{-0.356} \quad (0.5\% \leq C \leq 4.25\%)$$
$$\ln[R(k\Omega)] = -g_1 + g_2/T(K)$$
$$g_1 = 3.662 + 0.0195 \, C;$$
$$g_2 = 10,338 + 13.38 \, C \, (0 \leq C \leq 400 \text{ ppm})$$

Figure 17:
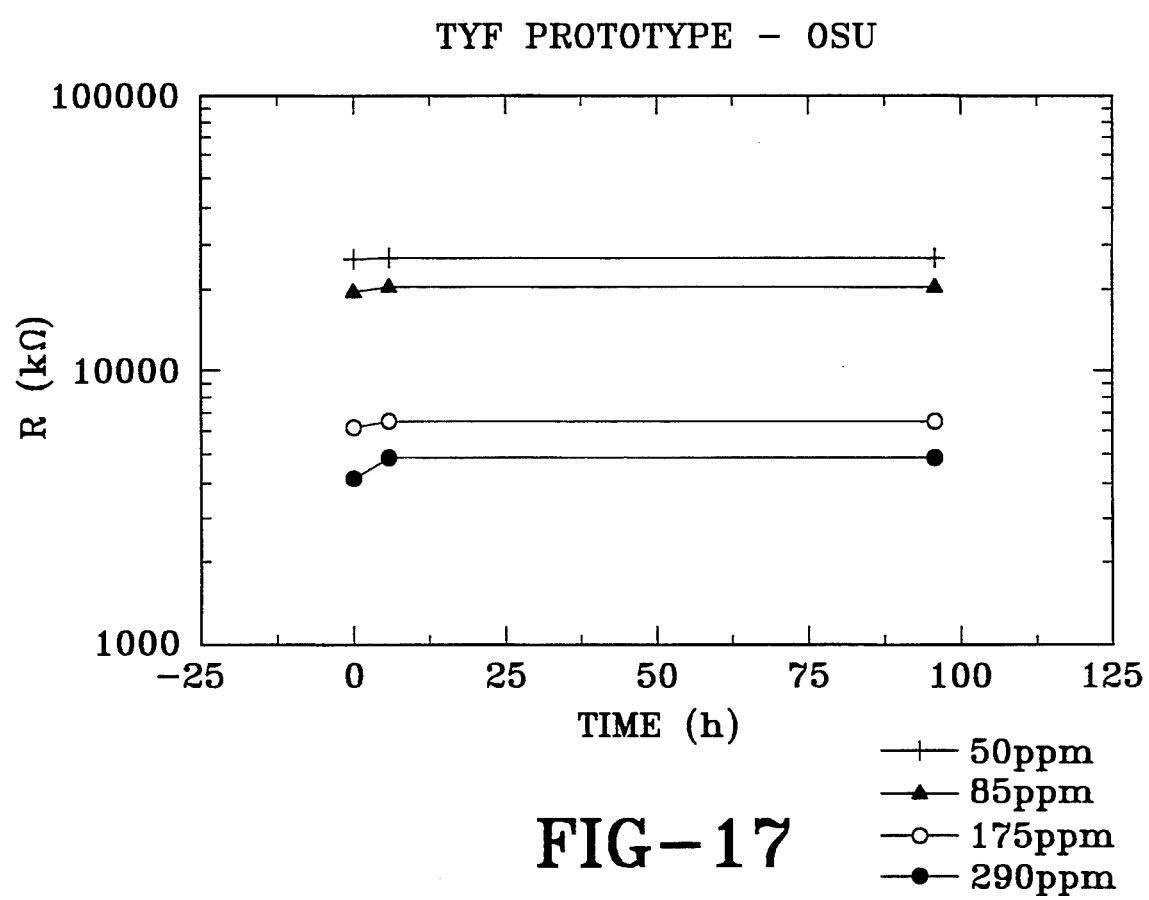
FIG. 17 is a graph showing time dependence of the resistance of prototypes when exposed to various levels of CO at 500° C. for extended periods.

In order to estimate the shelf-life of the TYF-based sensors, these were exposed to various levels of CO at a given temperature for uninterrupted long time periods, and the film resistance was monitored continuously. The constancy of film resistance over an extended period of time up to 100 h at a typical temperature of 500° C. (FIG. 17), shows an excellent chemical and mechanical stability of the sensor film in the real environments over an extended period.

Figure 18:
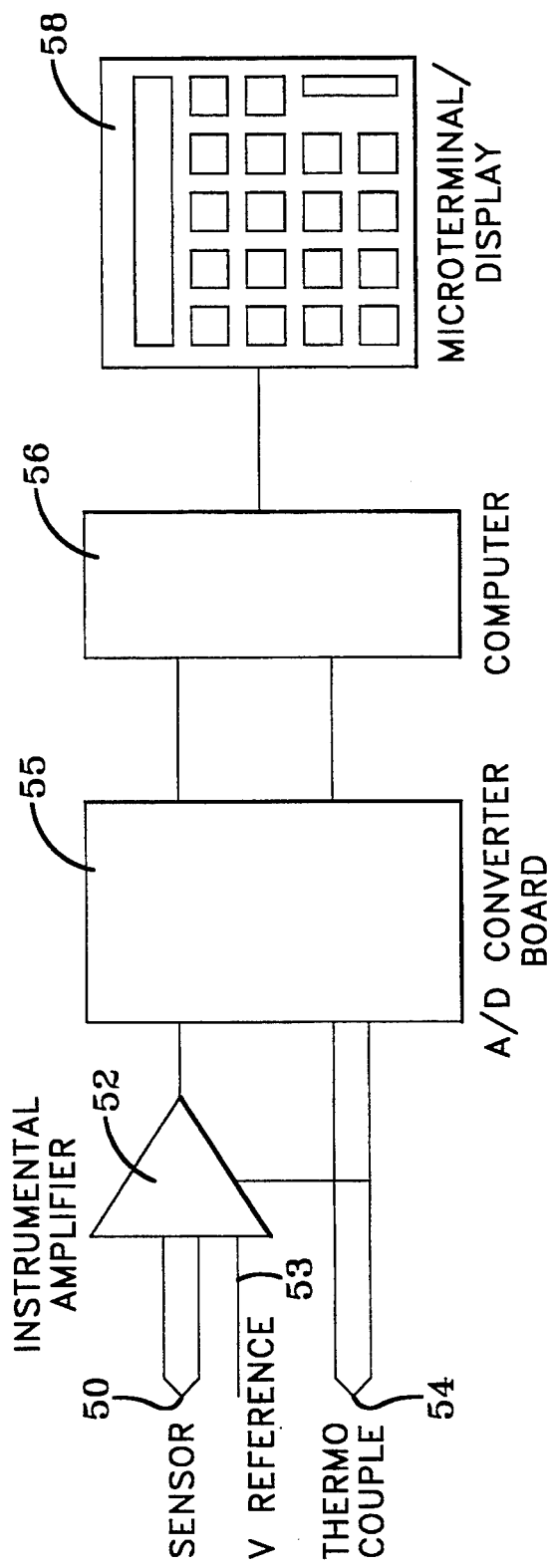
FIG. 18 is a CO sensor system block diagram.

FIG. 18 shows a block diagram of a CO sensor system with electronic interfacing employing the materials of the present invention. This system was designed for direct on-line reading and display of the CO contents in a flue gas stream. The CO sensor 50 is connected to the gain resistor inputs of the instrumentation amplifier 52, which has a reference voltage 53 applied to its input. The output of the amplifier is thus solely a known function of the sensor resistance. A type K thermocouple 54 is used to monitor the temperature in the immediate location of the sensor 50. These two signals pass through A/D converter 55 and are converted to digital numbers and sampled by the computer 56 once every second. The computer calculates the resistance of the sensor, the temperature and applies the generic parametric equations to determine the concentration of carbon monoxide (or CO—$H_2$ or $H_2$) in the immediate environment of the sensor. The quantities are then displayed and updated on the micro terminal 58. The device has been tested under simulated conditions by feeding known but arbitrary values for resistance and temperature. The displayed CO concentrations showed good agreement between the sensor output and the actual CO concentrations.

While certain preferred embodiments of the present invention have been disclosed in detail, it is to be understood that various modifications may be adopted without departing from the spirit of the invention or scope of the following claims.

We claim:

1. A sensor for sensing carbon monoxide and hydrogen in a mixture of gases comprising:
   a) a sensing ceramic comprising an anatase $TiO_2$;
   b) means disposed to pass an electric current through said ceramic;

c) means to measure changes in current characteristics when said ceramic is exposed to an atmosphere containing at least one of the gases hydrogen and carbon monoxide.

2. The sensor of claim 1 wherein said ceramic comprises anatase $TiO_2$ and $Y_2O_3$ and said sensor is selective to carbon monoxide.

3. The sensor of claim 2 wherein said $Y_2O_3$ is present within the range of 5 to 15 wt. %.

4. The sensor of claim 3 wherein said ceramic includes a catalytic metal.

5. The sensor of claim 3 wherein said ceramic includes up to 5 wt. % of a metal selected from the group consisting of iron and palladium.

6. The sensor of claim 1 wherein said ceramic comprises anatase $TiO_2$ and $Al_2O_3$ and said sensor is selective to hydrogen.

7. The sensor of claim 6 wherein said $Al_2O_3$ is present within the range of 5 to 15 wt. %.

8. The sensor of claim 1 wherein said ceramic comprises anatase $TiO_2$-10 wt. % $Y_2O_3$ and 2% Fe.

9. The sensor of claim 1 wherein said ceramic comprises anatase $TiO_2$-10 wt. % $Y_2O_3$ and 2% Pd.

10. An apparatus for sensing and determining the amount of carbon monoxide and hydrogen in a mixture of gases comprising, in combination,
a) a sensing ceramic comprising an amount of an anatase $TiO_2$ effective to selectively sense the presence of at least one of carbon monoxide and hydrogen gases in a mixture of gases exposed to said sensing ceramic;
b) a source of electric current connected to said sensing ceramic;
c) a first electronic circuit operatively connected to said sensing ceramic to provide a signal representing the electrical resistance of said sensing ceramic; and
d) a second electronic circuit operatively connected to said first electronic circuit to convert said resistance signal to a signal representing the amount of at least one of hydrogen or carbon monoxide gases in a gas mixture exposed to said sensing ceramic.

11. The apparatus defined in claim 10 wherein said sensing ceramic includes an amount of $Y_2O_3$ in the range of about 5 to 15% by weight.

12. The apparatus defined in claim 10 wherein said sensing ceramic includes an amount of $Al_2O_3$ in the range of about 5 to 15% by weight.

* * * * *